United States Patent
Hayashi et al.

(10) Patent No.: US 7,059,721 B2
(45) Date of Patent: Jun. 13, 2006

(54) MEDICAL DATA PROCESSING METHOD AND MEDICAL DATA PROCESSING SYSTEM

(75) Inventors: Norimasa Hayashi, Aichi (JP); Masunori Kawamura, Aichi (JP)

(73) Assignee: Nidek Co., Ltd., Aichi (JP)

(*) Notice: Subject to any disclaimer, the term of this patent is extended or adjusted under 35 U.S.C. 154(b) by 214 days.

(21) Appl. No.: 09/906,070

(22) Filed: Jul. 17, 2001

(65) Prior Publication Data

US 2002/0059301 A1  May 16, 2002

(30) Foreign Application Priority Data

Jul. 17, 2000 (JP) .......................... P2000-221064

(51) Int. Cl.
*A61B 3/14* (2006.01)
*A61B 3/00* (2006.01)
*G06F 7/00* (2006.01)

(52) U.S. Cl. ...................... 351/206; 351/200; 351/246; 707/1

(58) Field of Classification Search ................ 351/200, 351/206, 246; 358/403, 404, 426.05; 711/100, 711/118, 161, 162; 345/530–537, 543–548, 345/556–560; 707/2, 100–101, 204–205
See application file for complete search history.

(56) References Cited

U.S. PATENT DOCUMENTS

| | | | |
|---|---|---|---|
| 5,374,967 A * | 12/1994 | Hideshima et al. | 351/208 |
| 5,993,001 A * | 11/1999 | Bursell et al. | 351/212 |
| 6,181,837 B1 * | 1/2001 | Cahill et al. | 382/305 |
| 6,304,948 B1 * | 10/2001 | Motoyama et al. | 711/162 |
| 6,330,572 B1 * | 12/2001 | Sitka | 707/205 |
| 2001/0029505 A1 * | 10/2001 | Gaudette et al. | 707/102 |

* cited by examiner

*Primary Examiner*—Patricia Bianco
*Assistant Examiner*—John R Sanders
(74) *Attorney, Agent, or Firm*—Sughrue Mion, PLLC

(57) ABSTRACT

A medical data processing method includes the steps of inputting or obtaining image data, temporarily storing the inputted or obtained image data, and automatically deleting the temporarily stored image data in accordance with a predetermined delete condition.

4 Claims, 11 Drawing Sheets

FIG. 6

MEDICAL DATA PROCESSING METHOD AND MEDICAL DATA PROCESSING SYSTEM

BACKGROUND OF THE INVENTION

The invention relates to a medical data processing method and system for storing, managing and processing data, such as image data, obtained by a medical apparatus.

A medical data processing system is designed to store and manage and process image data and others, in the form of files, obtained by a medical apparatus such as a slit lamp microscope (called as "slit lamp") or a fundus camera by use of a personal computer (called as "PC"). In the medical data processing system, a storage folder is previously prepared on a patient-by-patient base in PC. In case of storing data, a storage folder for the patient (patient record) is designated each time so that the image data is inputted to and stored in the storage folder in the PC.

However, the existing procedure permits the storage only after the designation of a storage folder patient by patient, requiring time-consuming and troublesome operation. For example, in a case of mass examination for many patients, such orderly operation is very troublesome to delay the examination.

The existing procedure also stores such data sufficient to explain to patients and unnecessary to be stored, and the deletion of such data is time-consuming and troublesome. Without the deletion, the data unnecessarily occupy a memory capacity in a hard disk.

SUMMARY OF THE INVENTION

In view of problems encountered in connection with the related art, an object of the invention is to provide a medical data processing method and system with which medical data such as image data can be easily stored, managed and processed.

In order to solve the aforesaid object, the invention is characterized by having the following arrangement.

(1) A medical data processing method comprising the steps of:
inputting or obtaining image data;
temporarily storing the inputted or obtained image data; and
automatically deleting the temporarily stored image data in accordance with a predetermined delete condition.

(2) The method of (1), wherein the inputted or obtained image data includes first image data to which identification data is assigned, and second image data to which the identification data is not assigned, and the method further comprises the step of:
storing the first image data in a storage area corresponding to the identification data; and
wherein the step of temporarily storing includes temporarily storing the second image data in a temporary storage area.

(3) The method of (2), wherein the identification data includes patient data indicative of at least one of a patient name and a code number.

(4) The method of (1), further comprising the steps of:
displaying the temporarily stored image data; and
storing desired image data of the displayed image data in a designated storage area.

(5) The method of (4), wherein:
the step of temporarily storing includes temporarily storing the inputted or obtained image data while assigning ophthalmic examination data thereto, the ophthalmic examination data indicative of at least one of time of ophthalmic examination, an image format and an image capture mode, and
the step of displaying includes displaying the temporarily stored image data together with the ophthalmic examination data assigned thereto.

(6) The method of (1), wherein:
the delete condition includes a predetermined storageable amount; and
the step of deleting includes deleting the image data in order from the image data stored oldest if the predetermined storageable amount is exceeded.

(7) The method of (1), wherein:
the delete condition includes a predetermined storageable period; and
the step of deleting includes deleting the image data expiring the predetermined storageable period.

(8) A medical data processing method comprising:
inputting or obtaining image data;
storing first image data of the inputted or obtained image data, to which identification data is assigned, in a storage area corresponding to the identification data;
temporarily storing second image data of the inputted or obtained image data, to which the identification data is not assigned, in a temporary storage area;
displaying the second image data stored in the temporary storage area;
storing desired image data of the displayed image data in a designated storage area; and
automatically deleting the temporarily stored image data in accordance with at least one of a predetermined storageable amount and a predetermined storageable period.

(9) A medical data processing system comprising:
an input section which inputs or obtains image data;
a memory; and
a control section which temporarily stores the inputted or obtained image data in a temporary storage area within the memory, and automatically deletes the temporarily stored image data in accordance with a predetermined delete condition.

(10) The system of (9), wherein the control section stores first image data of the inputted or obtained image data, to which identification data is assigned, in a storage area corresponding to the identification data within the memory, and temporarily stores second image data of the inputted or obtained image data, to which the identification data is not assigned, in the temporary storage area.

(11) The system of (10), wherein the identification data includes patient data indicative of at least one of a patient name and a code number.

(12) The system of (9), further comprising:
a display, and
wherein the control section displays the temporarily stored image data on the display, and stores image data designated from the displayed image data in a designated storage area within the memory.

(13) The system of (12), wherein the control section temporarily stores the inputted or obtained image data in the temporary storage area while assigning ophthalmic examination data thereto, and displays the temporarily stored image data together with the ophthalmic examination data assigned thereto, the ophthalmic examination data indicative of at least one of time of ophthalmic examination, an image format and an image capture mode.

(14) The system of (9), wherein:
the delete condition includes a predetermined storageable amount; and
the control section deletes the image data in order from the image data stored oldest if the predetermined storageable amount is exceeded.
(15) The system of (9), wherein:
the delete condition includes a predetermined storageable period; and
the control section deletes the image data expiring the predetermined storageable period.
(16) A medical data processing system comprising:
an input section which inputs or obtains image data;
a memory;
a display; and
a control section that stores first image data of the inputted or obtained image data, to which identification data is assigned, in a storage area corresponding to the identification data within the memory, that temporarily stores second image data of the inputted or obtained image data, to which the identification data is not assigned, in a temporary storage area within the memory, that displays the temporarily stored image data, that stores image data designated from the displayed image data in a designated storage area within the memory, and that automatically deletes the temporarily stored image data in accordance with at least one of a predetermined storageable amount and a predetermined storageable period.

The present disclosure relates to the subject matter contained in Japanese patent application No. 2000-221064 (filed on Jul. 17, 2000), which is expressly incorporated herein by reference in its entirety.

BRIEF DESCRIPTION OF THE DRAWINGS

FIG. 6 is a view showing a screen that displays image data temporarily stored in a Queue folder;

DESCRIPTION OF THE PREFERRED EMBODIMENT

An embodiment of the invention will be described with reference to the accompanying drawings.

<Basic Structure of the System>

Figure 1:
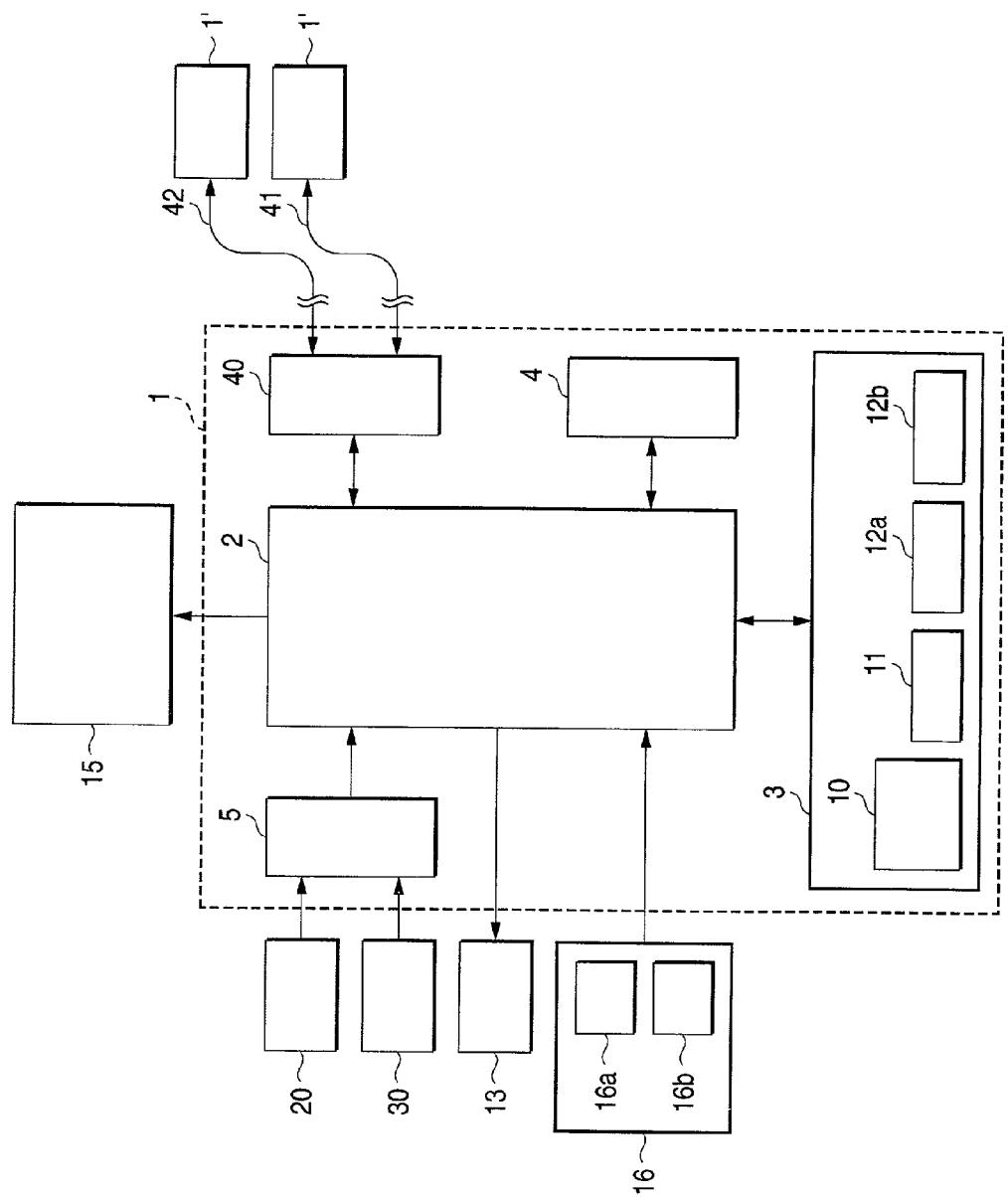
FIG. 1 is a schematic block diagram showing the structure of a medical data processing system.

FIG. 1 shows a structure of a medical data processing system for storing managing and processing ophthalmic data, such as image data, measured data and others obtained by an ophthalmologic apparatus.

Reference numeral 1 designates a PC, which includes, in the inside thereof, an arithmetic and control unit 2, an information recording and reproducing section (nonvolatile memory) 3 constructed by a hard disk drive, a RAM 4 (Random Access Memory), an input section 5, constructed by a video capture, for inputting image data to the PC 1, and a communication section 40 for exchanging (communicating) data with another PC 1'. The recording and reproducing section 3, RAM 4, input section 5 and communication section 40 are connected to the arithmetic and control unit 2.

A data processing software 10 (described later) is recorded (installed) in the inside of the recording and reproducing section 3, and when this software 10 is started up, the medical data processing system is ready for using.

Within the recording and reproducing section 3, storage folders (folders 12a, 12b . . . ) are prepared on a patient-by-patient basis, and image data for each patient is stored in the respective folder. If image data is inputted without the designation of the patient, the image data is stored in a Queue folder 11. These operations will be described in detail later. As the information recording and reproducing section 3, not only the hard disk drive but also DVD drive, a floppy disk drive, or the like may be used.

The input section 5 is connected to a fundus camera 20 and a slit lamp 30. An imaging system such as CCD camera, a digital camera (not shown) or the like for capturing (obtaining) images is preliminarily provided to each of the fundus camera 20 and the slit lamp 30, so that image data obtained by each imaging system is inputted via the input section 5 into the PC 1.

A communication section 40 is furnished with a modem and a LAN board, enabling mutual communications with other PCs 1' through an internet 41 or an LAN 42 (Local Area Network).

Reference numeral 13 designates a printer for outputting the inputted image onto a paper. Reference numeral 15 designates a display for which a general purposed display, such as a LCD or CRT monitor, can be used. Reference numeral 16 designates an operation section for issuing operation instructions to the PC 1 or the started software 10. As the operation section 16, a key board 16a and a mouse 16b are used.

<Structure of the Data Processing Software>

When the software 10 is started up, the arithmetic and control unit 2 reads the software 10 from the recording and reproducing section 3 and causes it to be resident in RAM 4. The software is mainly made up of four processing screens. The processing screens are respectively shown in FIGS. 2 to 5, and each of them will be explained.

(Patient List Screen)

Figure 2:
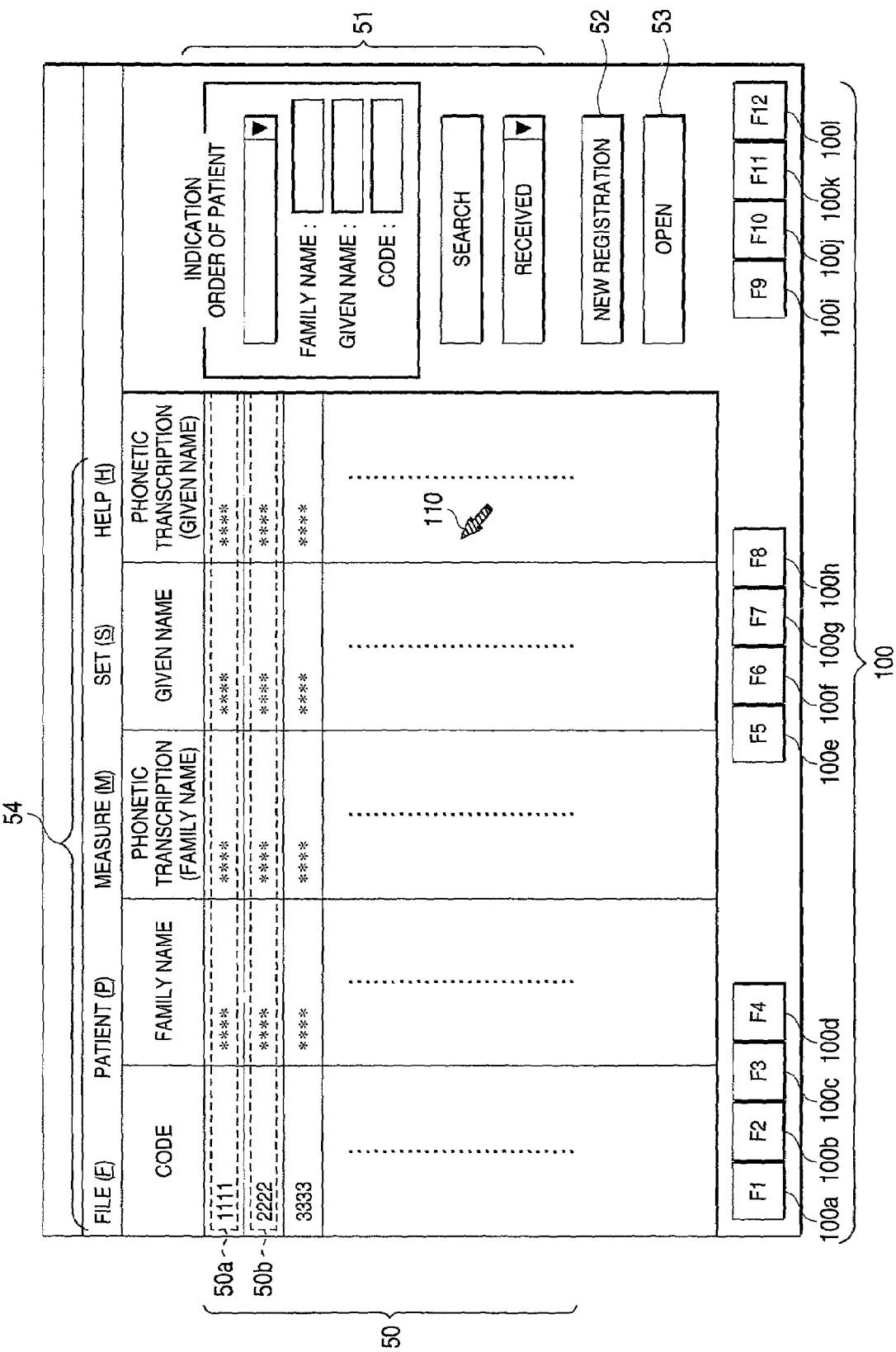
FIG. 2 is a view showing a patient list screen that is one of screens displayed when a data processing software is used.

When the software 10 is started up, a patient list screen is first displayed on the display 15 as viewed in FIG. 2. This screen serves as a main screen with which indication of a list of already registered patients, search for a patient, and receipt (registration) of a new patient, and the like can be executed. The list of registered patients is indicated in order as a patient 50a, a patient 50b . . . in a display column 50.

For each of the registered patients, a respective storage folder has been prepared within the recording and reproducing section 3. In the present embodiment, a holder 12a for the patient 50a and a holder 12b for the patient 50b have been prepared, respectively.

At the right side of the screen, a vertical row (a column) is provided, which includes a button (icon) group 51 for searching a registered patient, a registration button (icon) 52 for new registration, and an open (disclosure) button (icon) 53 for retrieving details of individual patient data. To use any of these buttons (icons), a cursor mark 110 shown on the display 15 is moved onto a desired button (icon) with the mouse 16b, and then an unillustrated button on the mouse 16b is clicked.

At the lower part of the screen, shortcut button (icon) group 100 is provided so that 12 pieces of shortcut buttons (icons) 100-a to 100-1 can be used. These shortcut buttons 100-a to 100-1 correspond respectively to tasks assigned to function keys (F1 to F12) of the key board 16a.

To the function keys of the key board 16a, various functions (tasks), such as measurement, screen change, etc. are assigned as shortcut keys to enable these tasks with a single operation of the keyboard. The task assignment to the function keys (shortcut buttons 100) may be set arbitrarily to match with user's convenience.

The shortcut buttons (icons) provided in this embodiment include a button (icon) 100a for movement to the main screen, a button (icon) 100b for displaying the patient list, a button (icon) 100c for obtaining image data from the fundus camera 20, a button (icon) 100d for obtaining image data from the slit lamp 30, a button (icon) 100e for displaying, in a thumbnail fashion, all image data stored in the Queue folder 11, and a button (icons) 100f for outputting selected image data using the printer 13. In this embodiment, no task is assigned to the remaining buttons (icons) 100-g to 100-1.

At the upper part of the screen, a menu bar 54 is displayed, which contains items of "File", "Patient", "Measure", "Set", and "Help", and main functions (such as switch of a displayed screen) may be selected and used via this menu bar 54.

(Registration Screen)

Figure 3:
FIG. 3 is a view showing a registration screen that is one of the screens displayed when the data processing software is used.

FIG. 3 shows a screen with which a new patient is registered, or registered patient data is displayed. This registration screen can be displayed upon operation of the registration button 52 or the open button 53 shown in FIG. 2. At the left side of the registration screen, buttons (icons) are displayed in a hierarchical structure view (tree view 84), which respectively identify collected medical data such as image data obtained till now and measured data, and their stored contents or conditions are visually grasped.

A patient data registration screen 60 is used to register a new patient. Input items of the patient data are "Name", "Phonetic transcription", "Sex", "Birthday", "Code", "Day of first medical examination", "Address", and "Tel. No.". Reference numeral 61 designates an OK button (icon) for executing registration, and 62 is a cancel button (icon) for canceling registration. By performing a new registration, storage folders are prepared (recorded) in the information recording and reproducing section 3 correspondingly to the number of the new registration. (Image input screen)

Figure 4:
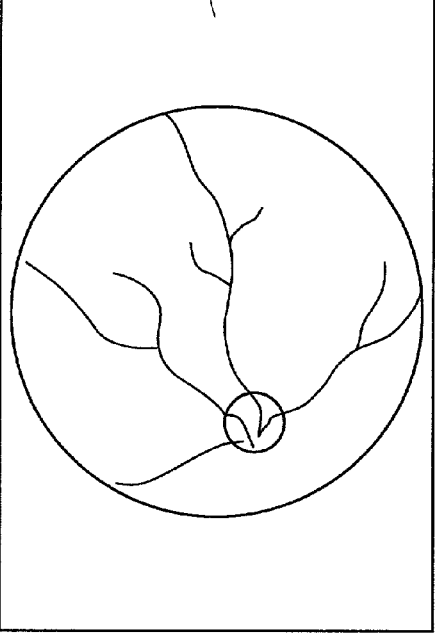
FIG. 4 is a view showing an image input screen that is one of the screens displayed when the data processing software is used.

FIG. 4 shows an image input screen with which patient's eye image data obtained by the fundus camera or the slit lamp 30 is input into the PC 1.

Reference numeral 70 designates a main image box, in which a latest inputted image is shown largely. 71 is a thumbnail indication box, in which the inputted images are displayed sequentially as thumbnail images 70a, 70b.

In case where a plurality of thumbnail images are displayed on the thumbnail box 71, the selection of one among these images will cause the selected thumbnail image to be displayed on the main image box 70 in an enlarged manner.

Reference numeral 73 designates a set button (icon) group for setting data of eye examination with respect to the inputted image. With the set button group, date of eye examination, designation of left or right eye, an image format, and an image capture mode can be selected and set. As to the image format and the image capture mode, several options (selection items) are preliminarily registered to form a pull-down menu (for example, in a case of the image format, JPEG image High quality, JPEG image Low quality, etc., and in a case of the fundus camera, color fundus image, FAG fundus image, ICG fundus image, etc.), and any of them is selected and set using the pull-down menu.

The image of patient's eye is inputted from the ophthalmologic apparatus (the fundus camera 20 or the slit lamp 30) by clicking an input button (icon) 74. The input operation for the image data may be carried out using a joystick or a foot switch (both not shown) provided in the ophthalmologic apparatus other than the use of the input button 74. Reference numeral 75 is a finish button (icon) for finishing the transfer operation, and returning to the latest previous operation screen.

(Image Storage Screen)

Figure 5:
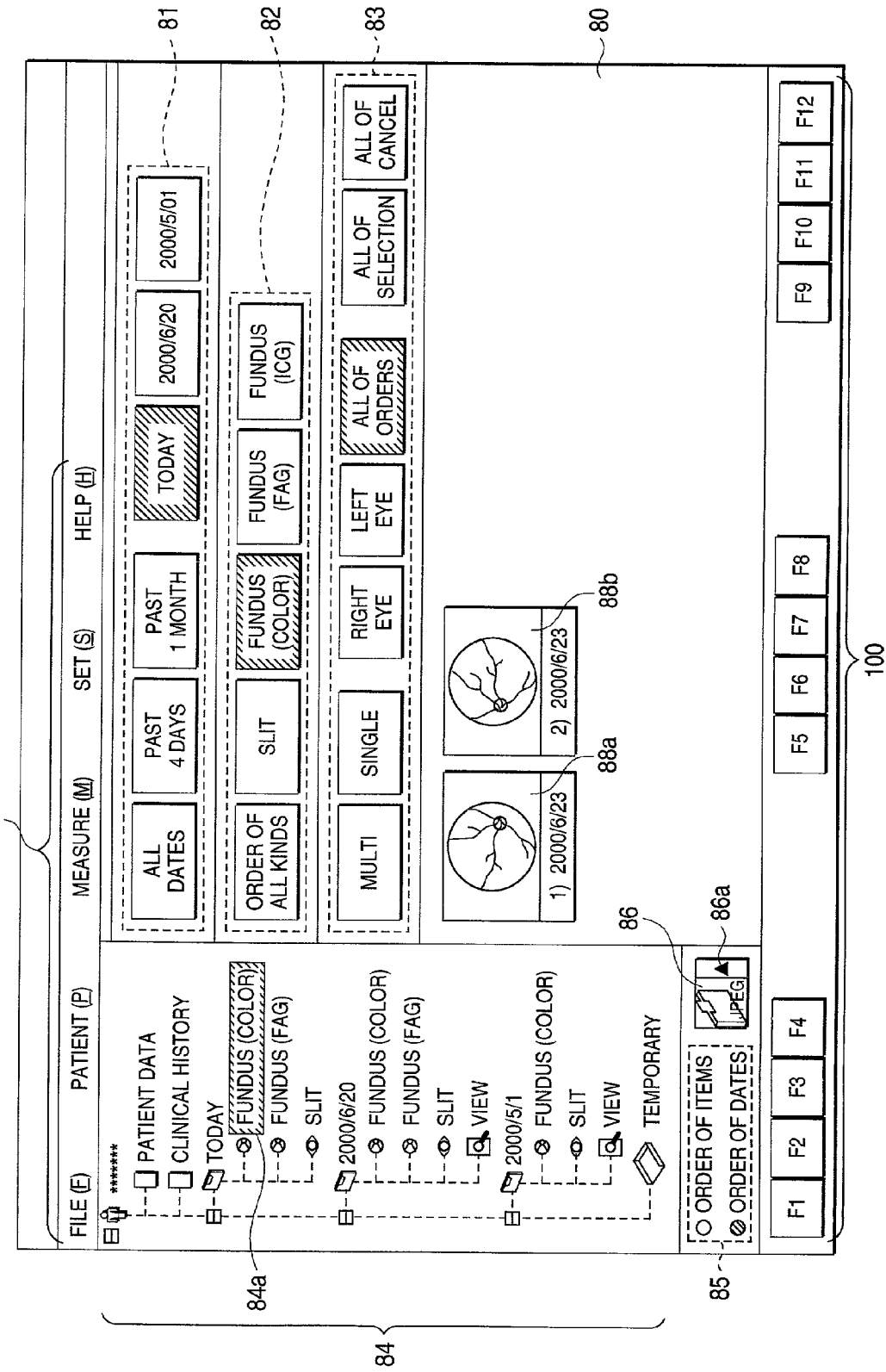
FIG. 5 is a view showing an image storage screen that is one of the screens displayed when the data processing software is used.

FIG. 5 shows an image storage screen in which the image data stored in the storage folder is displayed.

At the left side of the screen, various kinds of data stored in the folder are displayed in a hierarchical structure view (tree view 84) in date order or in item order (a fundus image, a slit image, etc.). a radio button 85 may be used to alter the hierarchical structure.

By selecting a button (icon) (for example, a fundus image button (icon) 84a) displayed in the tree view 84, the image data corresponding to the selected button (icon) is displayed as thumbnails 88a, 88b in the screen 80.

A plurality of buttons (icons), set in a date selection tool bar 81 for selecting a date of an image to be displayed, a kind selection tool bar 82 for selecting a kind of an image to be displayed, and a control tool bar 83 for designating a displaying condition such as a left or right eye, maybe selectively used to select a thumbnail image to be displayed on the display screen 80.

Reference numeral 86 is an output button (icon) for outputting the thumbnail image displayed on the display screen 80 (for usage other than the image data to be used in the software 10). Beside the output button 86, a button (icon) 86a for a pulling down menu is provided, and by clicking the button 86a, the output type (form) may be set variously.

Figure 7:
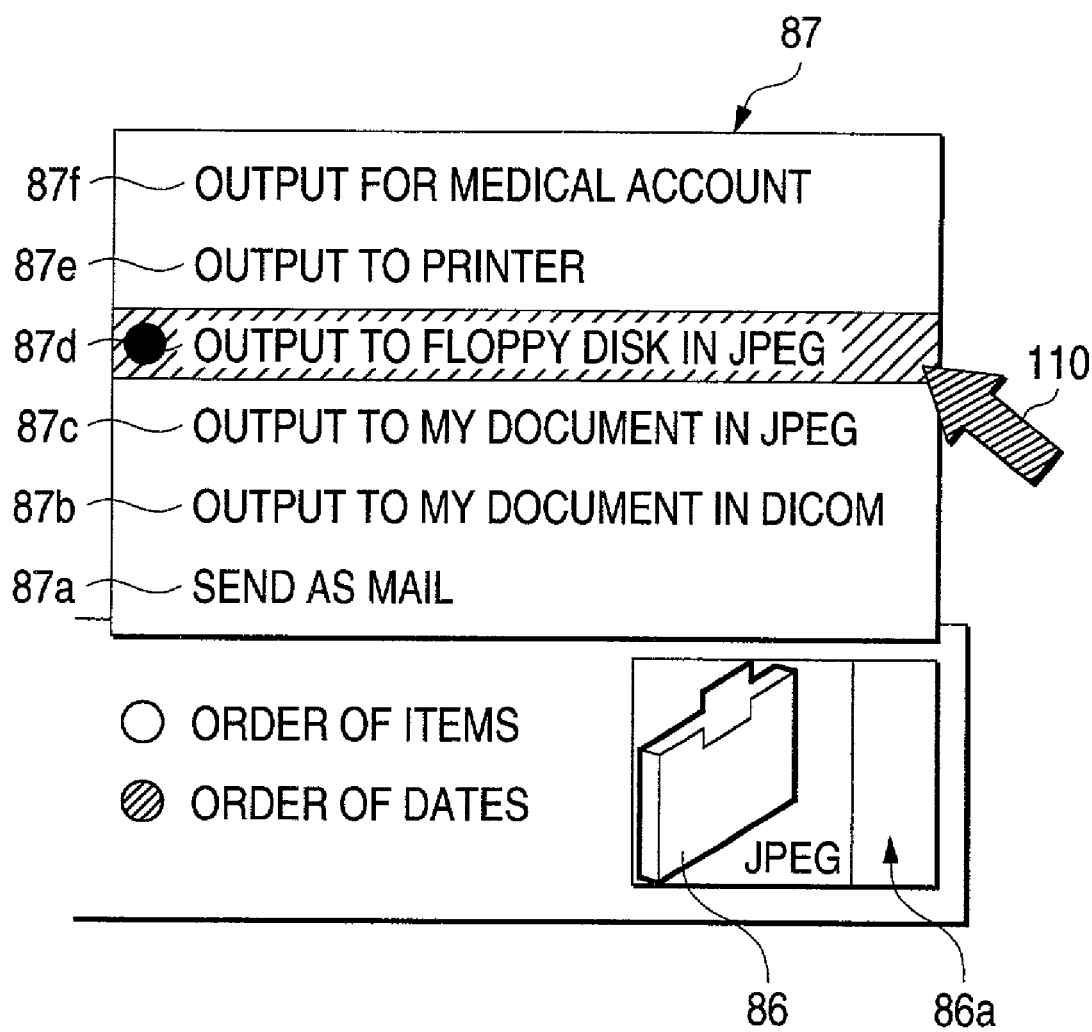
FIG. 7 is a view showing a state in which a pull-down menu is displayed.

FIG. 7 shows a pull-down menu 87 displayed using the button 86a. Items for output type of the image data include a mail sending item 87a for selecting and setting output type of the image file as an appending file to a general purposed mail software, a DICOM (Digital Imaging and Communications in Medicine) output item 87b for selecting and setting output type of the image data as a DICOM data to a My Document folder, a JPEG output item 87c for selecting and setting output type of the image data as JPEG data, which is one kind of image formats, to the My Document folder, an FP output item 87d for selecting and setting output type of the image data to a floppy disk in the JPEG data, a printer output item 87e for selecting and setting output type of the image data to the printer 13, and an account output item 87f for selecting and setting output type of the image data as a medical account.

By selecting any one of the output items 87a to 87f, the appearance of the output button 86 is changed to correspond to the selected output item. (In FIG. 7, the icon corresponding to the FP output item 87d is shown.)

Figure 6:
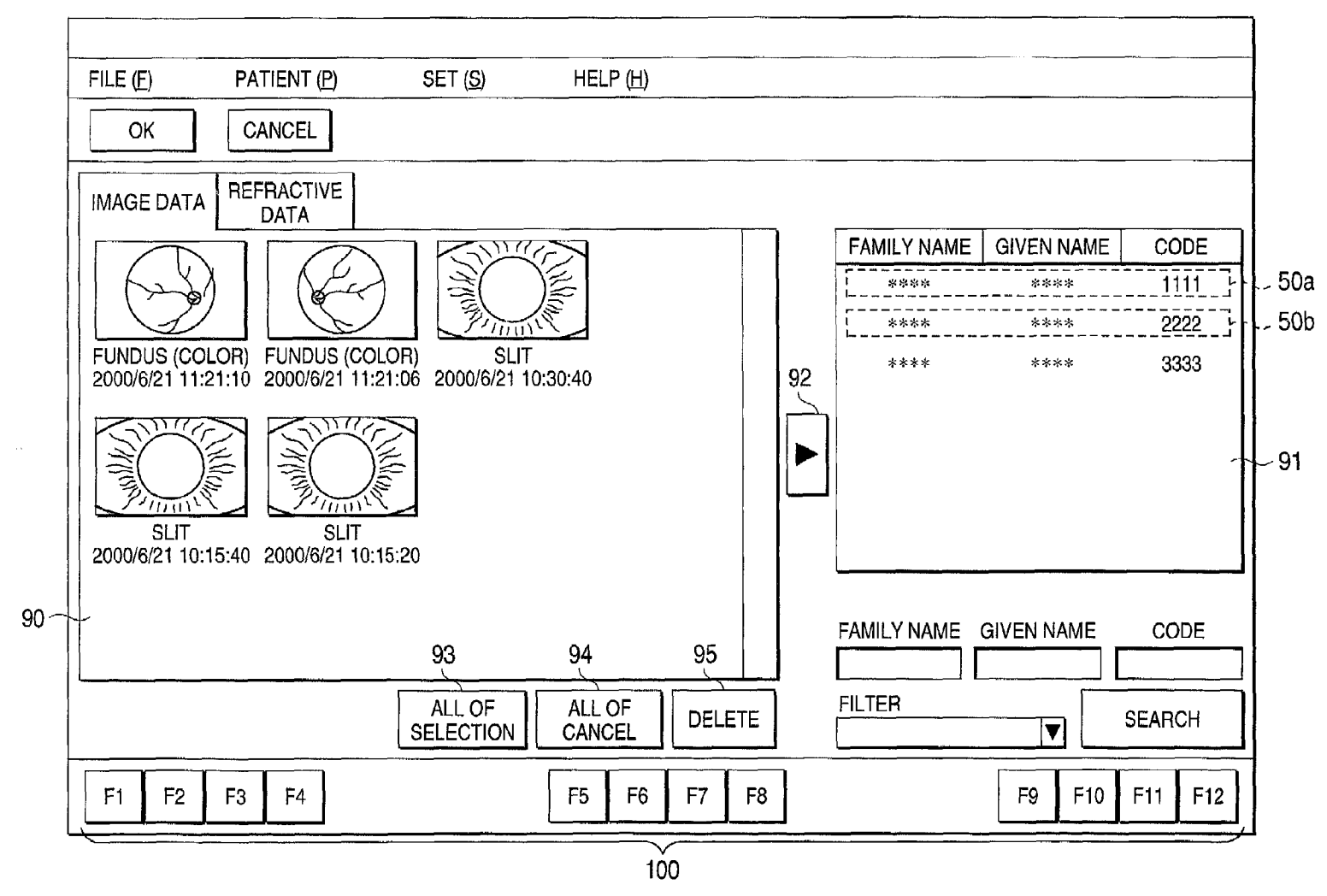

FIG. 6 is a screen for displaying image data temporarily stored in the Queue folder 11.

The image data temporarily stored in the Queue folder 11 is displayed in a thumbnail fashion on an image display screen 90. At the right side of the image display screen 90, a patient list screen 91 is provided, which displays patients 50a, 50b preliminarily registered. The image data displayed on the image display screen 90 can be moved to and stored in the folder by executing a drag-and-drop of the image data to the corresponding patient 50a, 50b.

Reference numeral 92 designates a moving button (icon) Image data to be moved and a patient to which the image data is to be moved may be selected, and subsequently the moving button 92 may be used to move and store the image data into designated folder similarly to the drag-and-drop operation.

Reference numeral 93 designates an all-selection button (icon) for selecting all image data displayed on the image display screen 90. Numeral 94 is an all-cancellation button (icon) for canceling selection of the selected image data. 95 is a deleting button (icon) for deleting the selected image data. With respect to the image data displayed on the image display screen 90, though not using the deleting button 95, but on the basis of the number of set pieces or a set period of time, the data are automatically deleted in order of older ones from the Queue folder 11, so that deleted data no more appear on the image display screen 90. An upper limited piece number of image data to be registered or a registration period can be determined using the setting items of the menu bar 54.

Reference will be made to the operation of the medical data processing system having the above mentioned structure. First of all, a case of designating a storage folder and storing image data will be explained.

In the present embodiment, explanation will be made to operation of inputting a fundus image from the fundus camera 20.

The software 10 is started up. One of the registered patients is selected using the main screen shown in FIG. 2 (herein, the patient 50a is selected), and then the button 100-c is clicked to display the image input screen shown in FIG. 4 to input the image from the fundus camera 20 or the slit lamp 30.

Prior to the image input, the set button group 73 is used to preliminarily select and set data for eye examination, such as date of eye examination (photographing date), designation of left or right eye, an image format, an image capture mode and others.

In the case of the fundus camera 20, a patient sits in front of the fundus camera 20, and the fundus camera 20 is moved to be aligned with the patient's eye. After alignment (positional adjustment) between the patient's eye and the fundus camera 20 is completed, the input button 74 is clicked to obtain and input the fundus image into the PC 1. The inputted image data is stored in the folder 12a, and concurrently displayed on the main box 70 and also on the thumbnail display box 71 as a thumbnail type image.

To the inputted image data, the patient's data inputted during the patient registration, the data for eye examination set using the set button 74 prior to the image data input, and image input time data are allocated (attached) automatically. Therefore, various data is displayed at four corners of the image data displayed on the main image box, and the date of the eye examination is displayed on the thumbnail image data (the image data 70a, 70b) (see FIG. 4).

After the input of a required fundus image(s) is complete, the finish button 75 is clicked to go back to the latest previous operation screen (in this case, the main screen) and finish the image input.

In case that image data stored in the folder 12a is to be reviewed, the patient is selected using the main screen, and the open button 53 is clicked, whereby the registration screen 60 shown in FIG. 3 is displayed. Subsequently, a desired image button (icon) is selected from the tree view 84 displayed at the left side of the screen. Upon selection of the image button is selected, the image storage screen shown in FIG. 5 is displayed.

Here, in case that the image data stored in the folder 12a is outputted (data outputting process) to other than the software 10, the image data displayed on the display screen 80 may be made drag-and-drop onto the output button 86.

Figure 8:
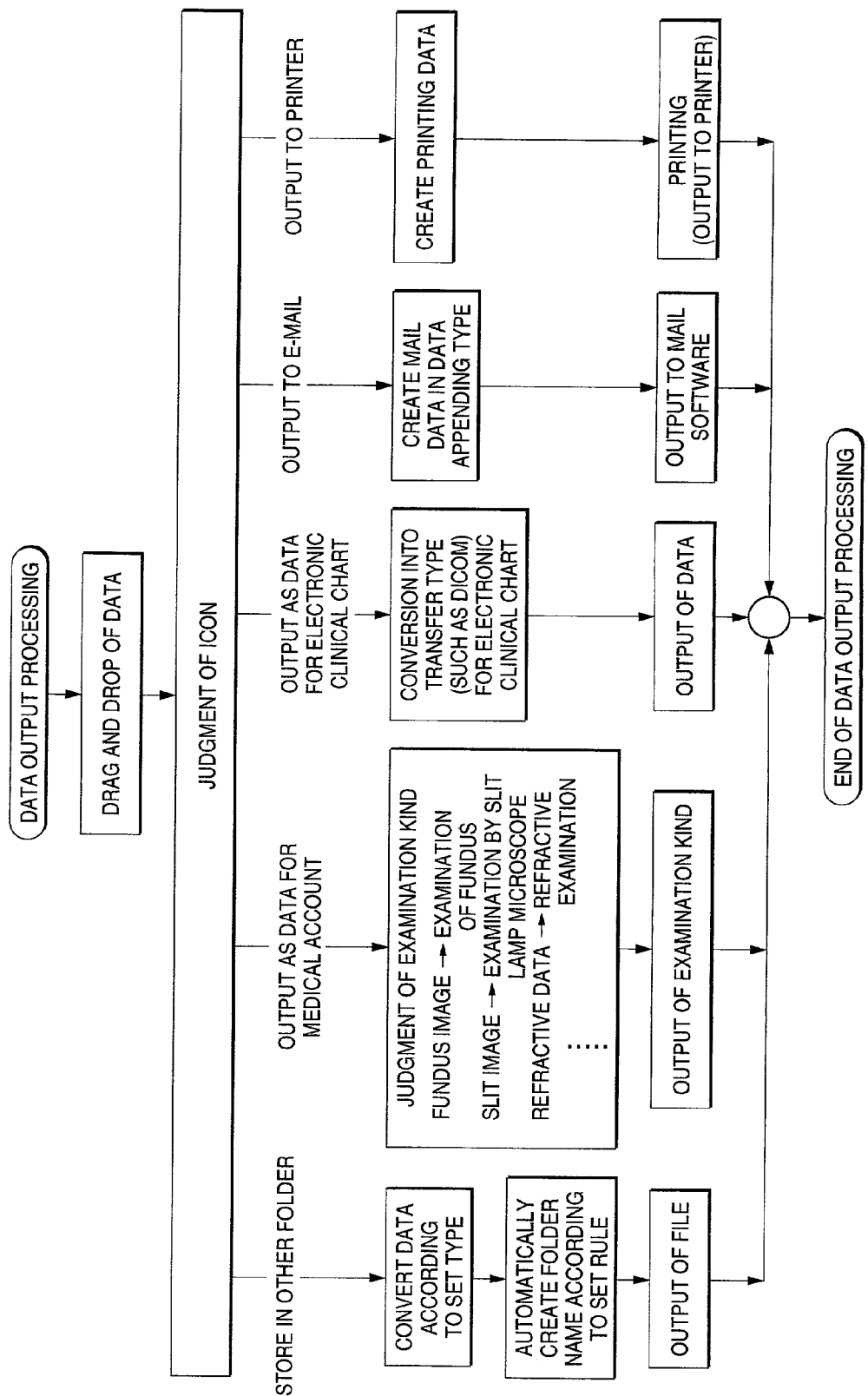
FIG. 8 is a flow chart showing a sequence of a data output process.

FIG. 8 is a flow chart showing a sequence of the data output process. As shown in the flow chart, if the image data (the thumbnail image) displayed on the display screen 80 is made drag-and-drop onto the output button 86, the selected output button 86 is judged (the icon judgment). A targeted kind of the output button 86 is previously selected using the pull-down menu 87 in FIG. 7. In case of the output button 86 indicative of the selection of the mail sending item 87a, the image data is outputted as an appended file to the mail software. By appending the image data to E-mail, the image data can be sent to other PC 1' through the internets 41, LAN 42, etc.

In case that DICOM output item 87b has been selected, the image data is outputted, as DICOM data, to the My Document folder prepared in the recording and reproducing section 3.

In case that JPEG output item 87c, FP output item 87d or the like has been selected as the output button 86, the image data is output to another folder (or a floppy disk) preliminarily determined, and in case that the printer output item 87e has been selected, the image data is output to the printer 13.

Further, in case that the account output item 87f has been selected as the output button 86, data (examination assorting data showing an apparatus or the like used in the examination) necessary for the medical account is extracted from the eye examination data attached to the image data, and outputted as data for the medical account. This makes it possible for a medical account software to read information, such as points of health care insurance, without a manual input.

Thus, by only performing the same operation (drag-and-drop of image onto the output button 86), various tasks can be carried out in a short time.

Figure 9A:
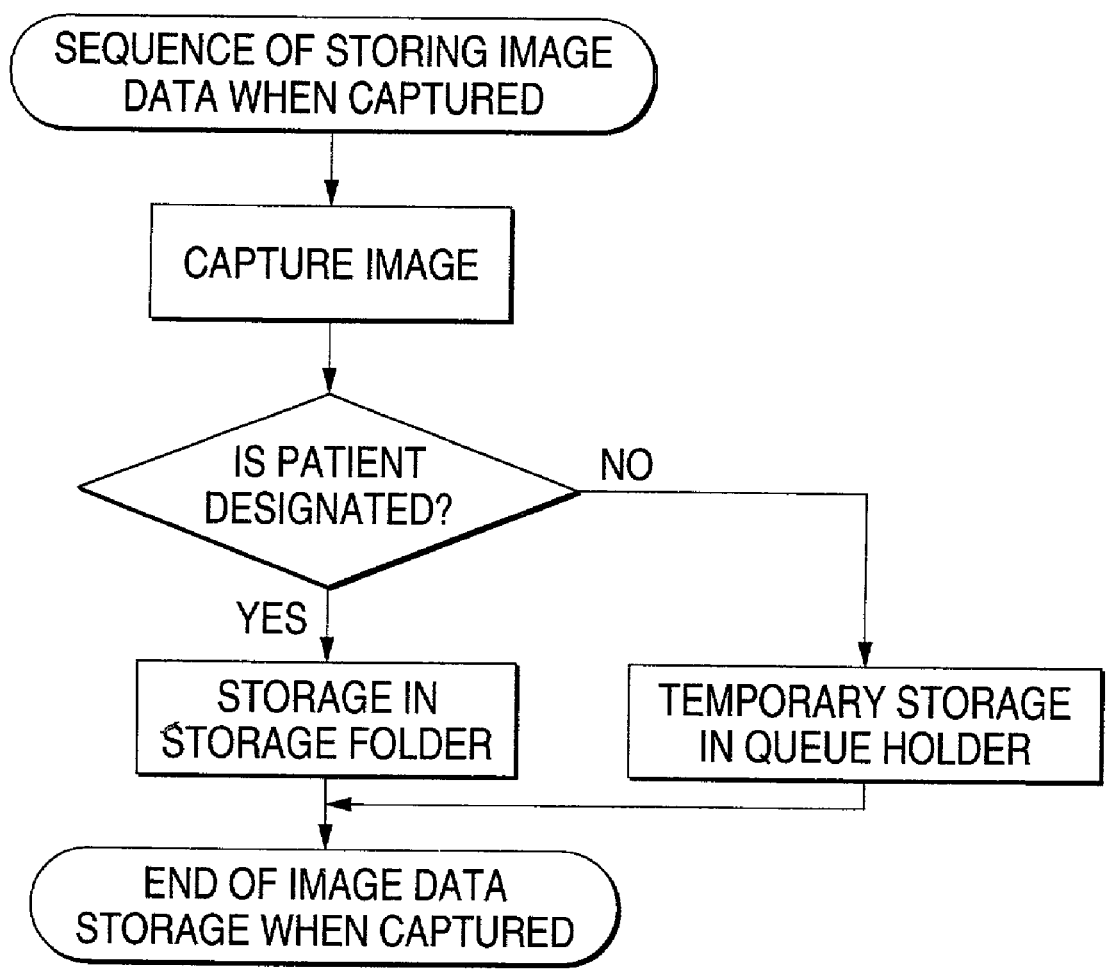
FIGS. 9A to 9C are flow charts showing sequence of an image storing method.
Figure 9B:
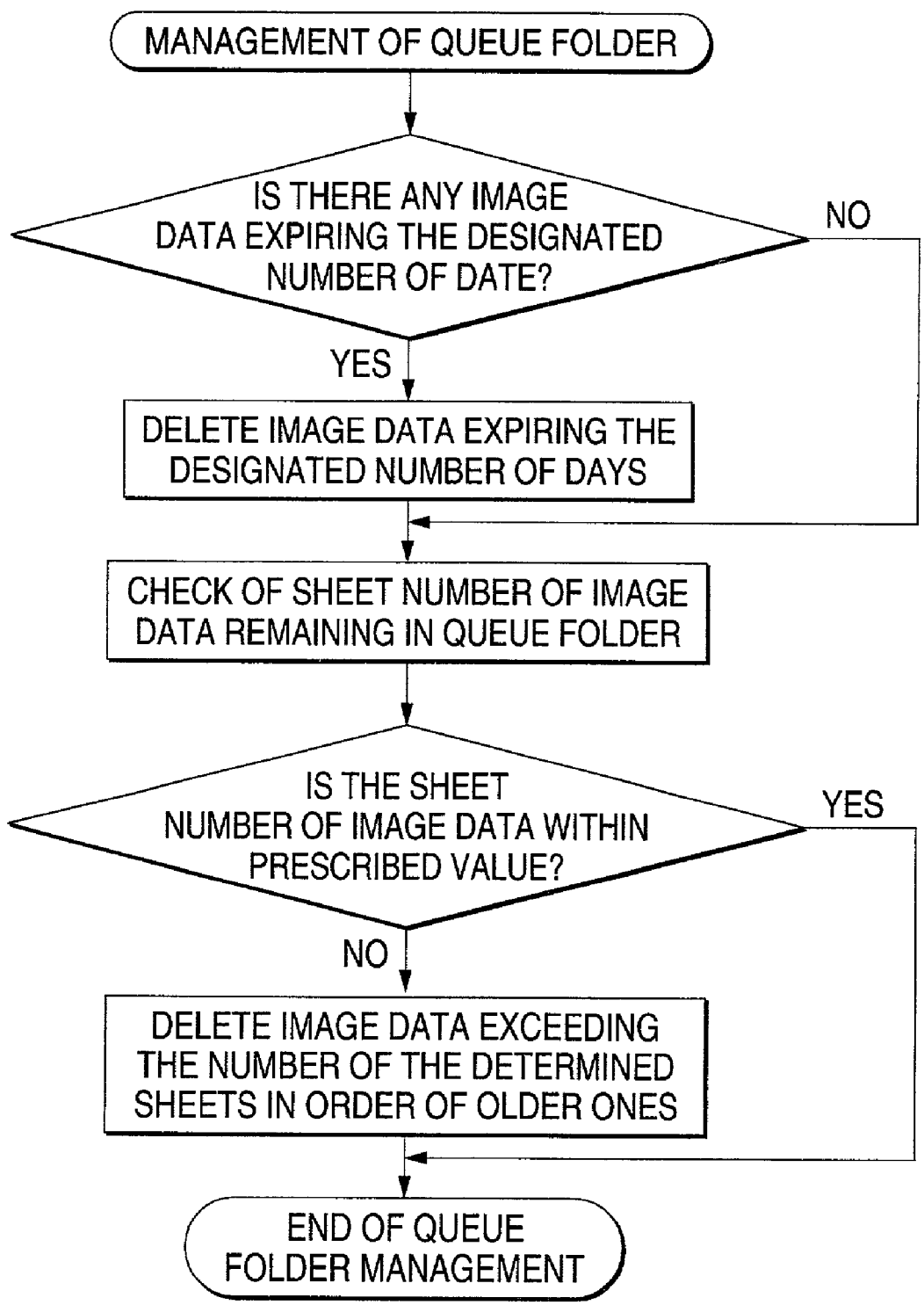
Figure 9C:
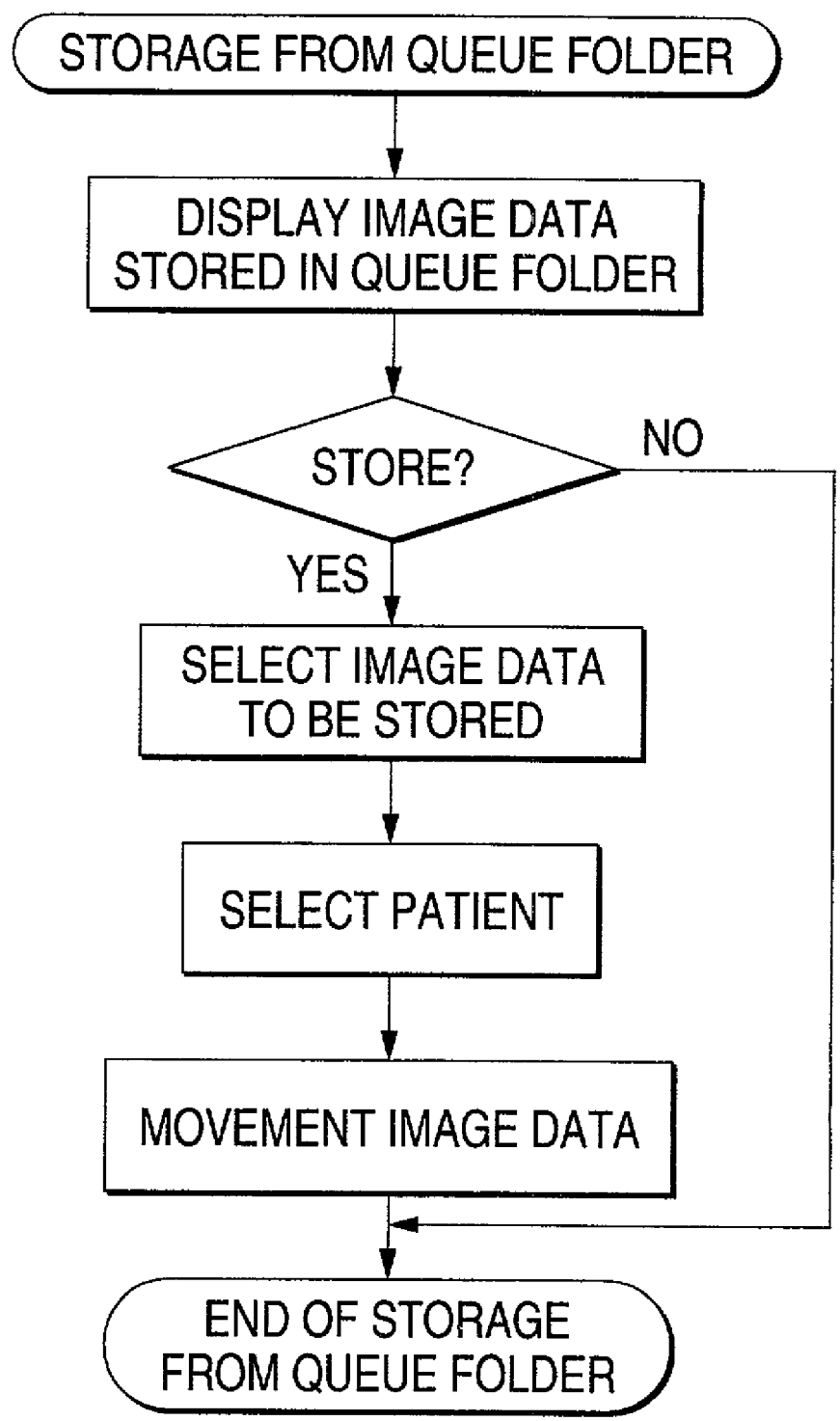

Next, reference will be made to a case of inputting the image data without designating a patient. If the image is inputted from the fundus camera 20 or the slit lamp 30 without designating the patient in the image input screen in FIG. 4, the inputted image is temporarily stored as queue data (storage awaiting data) in the Queue folder 11 as shown in the flow chart of FIG. 9A. The image data temporarily stored in the Queue folder 11 is automatically deleted (disappears) in succession in order of data expiring a previously designated number of days (the number of storageable days, for example 3 days) as shown in the flow chart of FIG. 9B. If pieces of the image data temporarily stored in the Queue folder 11 exceed the number of determined pieces (storageable amount, for example 100 pieces), the image data exceeding the number of the determined pieces is deleted in order of older ones.

Since the data temporarily stored in the Queue folder 11 is automatically deleted when the data becomes out of the determined storage condition, a labor of specially deleting unnecessary data may be saved. It is free from a problem of wastefully consuming the memory capacity of the hard disk. That is, images obtained by each ophthalmologic apparatus involve images unnecessary to be stored in the storage folder. For example, several sheets of images are sometimes obtained only for the purpose of explaining to the patient. In this case, the explanation is given to the patient while referring to the explaining-purpose image largely displayed on the main image box 70 of the image input screen shown in FIG. 4 so as to explain to the patient. If the image data unnecessary to be stored is left as it is, the image data will be deleted as mentioned above.

In case many and unspecified patients are examined at once in mass medial examination and many images are stored, it is troublesome to designate patients one by one for data storage. Also in this case, the temporary storage in the Queue folder 11 without designating patients is convenient.

If necessary image data is selected from the image data temporarily stored in the Queue folder 11, and stored in the folder, the image display screen 90 shown in FIG. 6 is displayed, and then image data desired to be stored is selected. The drag-and-drop of the selected image data onto the patient list (patient 50*a*, 50*b* . . . ) displayed on the patient list screen 91 can move and store the image data in place.

Thus, by providing the Queue folder 11, storing operation and deleting operation can be dispensed with, and the operator is free from troublesome and time-consuming operation. In addition, since all of the image data is not stored, a capacity of a recording medium (in this embodiment, the information recording and reproducing section 3) is not wastefully consumed.

It is, as mentioned above, possible to move and store the image data temporarily stored in the Queue folder 11, but the software 10 is programmed such that the image data once stored in the storage folder cannot be moved to other places (folders) within the software 10. Accordingly, such an error can be eliminated that image data of a patient is put into another patient's folder.

In the embodiment, the present invention has been described with reference to an example of the ophthalmic apparatus, but the present invention should not be restricted thereto, and can be applied to various medical apparatuses that can obtain an image of a disease part or photographs the disease part, and that can obtain measured data.

As described above, according to the invention, since it is unnecessary to select or delete medical data each time, the storage, management and process for the medical data can be easily carried out.

What is claimed is:

1. An image managing system for managing image data captured by an ophthalmologic camera apparatus, the image managing system comprising:

a first memory which stores the image data with imaging condition data into a patient's folder, wherein the patient's folder is a new folder that is prepared in the first memory by registering a new patient, wherein the image data with imaging condition data in the patient's folder is inhibited from being moved to another patient's folder;

a second memory which temporarily stores the image data with the imaging condition data when neither the patient's folder nor the another patient's folder has been designated;

means for directly storing the image data with the imaging condition data into the patient's folder in the first memory when a user designates the patient's folder when capturing the image data, and for directly storing the image data with the imaging condition data into the second memory, temporarily, when the user does not designate either the patient's folder or the another patient's folder when capturing the image data;

means for moving the image data with the imaging condition data stored temporarily in the second memory to the patient's folder in the first memory, when instructed by the user, the moving means comprising display means for displaying the image data with imaging condition data which is temporarily stored in the second memory in thumbnail form, and displaying a list of folders in the first memory; and means for automatically deleting the temporarily stored image data with the imaging condition data when a predetermined storageable amount for the second memory is exceeded or automatically deleting the temporarily stored image data with the imaging condition data when a predetermined storageable period for the second memory expires.

2. The image managing system according to claim 1, further comprising:

means for transmitting the image data with the imaging condition data stored in the patient's folder in the first memory to another apparatus through communicating means.

3. The image managing system according to claim 1, wherein the image data stored in the patient's folder is displayed in a tree view while being branched into every date of imaging of the image data.

4. The image managing system according to claim 1, wherein the image data stored in the patient's folder is displayed in a tree view while being branched into every type of the image data.

* * * * *